US00RE34780E

United States Patent [19]

Trenconsky et al.

[11] E Patent Number: Re. 34,780

[45] Reissued Date of Patent: Nov. 8, 1994

[54] ELECTROSURGICAL CONDUCTIVE GAS STREAM EQUIPMENT

[75] Inventors: Robert P. Trenconsky, Elizabeth, Colo.; Carol A. Bertrand, Cambridge, Mass.; Robert A. Weiss, Waconia, Minn.

[73] Assignee: Birtcher Medical Systems, Inc., Irvine, Calif.

[21] Appl. No.: 838,375

[22] Filed: Feb. 19, 1992

Related U.S. Patent Documents

Reissue of:

[64] Patent No.: 4,901,719
Issued: Feb. 20, 1990
Appl. No.: 224,485
Filed: Jul. 26, 1988

U.S. Applications:

[63] Continuation-in-part of Ser. No. 849,950, Apr. 8, 1986, Pat. No. 4,781,175.

[51] Int. Cl.[5] ..... A61B 17/39

[52] U.S. Cl. ..... 606/49; 219/121.5; 219/121.51; 439/194

[58] Field of Search ..... 606/41, 42, 45, 49; 439/194, 195; 219/121.5, 121.51, 121.52, 74, 75

[56] References Cited

U.S. PATENT DOCUMENTS

| | | | |
|---|---|---|---|
| 2,376,265 | 5/1945 | Meredith | 219/75 |
| 2,828,747 | 4/1958 | August | 219/75 |
| 3,158,730 | 11/1964 | Hill | 219/75 |
| 3,690,567 | 9/1972 | Borneman | 219/121.51 |
| 4,040,426 | 3/1977 | Morrison, Jr. . | |
| 4,057,064 | 4/1977 | Morrison, Jr. et al. . | |
| 4,060,088 | 5/1977 | Morrison, Jr. et al. . | |
| 4,682,005 | 7/1987 | Marhic | 219/75 |
| 4,781,175 | 11/1988 | McGreevy et al. | 606/49 |

FOREIGN PATENT DOCUMENTS

| | | |
|---|---|---|
| 1014995 | 11/1965 | United Kingdom . |

*Primary Examiner*—Lee S. Cohen
*Attorney, Agent, or Firm*—John R. Ley

[57] ABSTRACT

An electrosugrical unit for conducting a predetermined ionizable gas in a jet stream to the tissue at a predetermined flow rate sufficient to clear natural fluids from the tissue and to substantially expose the tissue stroma and for exposing the gas to an electrical radio frequency energy to ionize the gas in conductive pathways in the gas jet stream. The unit includes a nozzle which is releasably connected to a handle for easy manipulation by a surgeon with the nozzle including means for supporting an electrode in an optimal position for initiation of the ionization of the gas. Also, a connecting system is disclosed for connecting the hose on which the handle is mounted to a gas delivery apparatus and supply or electrical energy which permits the hose to rotate while maintaining a positive hermetic seal to prevent the hose from kinking during use by a surgeon.

40 Claims, 5 Drawing Sheets

ELECTROSURGICAL CONDUCTIVE GAS STREAM EQUIPMENT

Matter enclosed in heavy brackets [ ] appears in the original patent but forms no part of this reissue specification; matter printed in italics indicates the additions made by reissue.

CROSS REFERENCE TO RELATED APPLICATION

This application is a Continuation-in-Part of copending application Ser. No. 849,950 filed Apr. 8, 1986, now U.S. Pat. No. 4,781,175 and entitled Electrosurgical Conductive Gas Stream Technique of Achieving Improved Eschar for Coagulation which is of common ownership with the present application, the disclosure of which is hereby incorporated by reference.

BACKGROUND OF THE INVENTION

1. Field of the Invention

This invention relates to electrosurgery, and more particularly to a new and improved electrosurgical technique for achieving coagulation or a hemostatic effect, i.e. fulguration and desiccation, by conducting radio frequency (RF) electrical energy through a conductive inert gas stream to the tissue. In addition, the present invention relates to an electrosurgical fulguration arcing technique of creating an eschar and tissue effects offering a substantially improved capability for coagulation. Further still, the present invention relates to an electrosurgical non-arcing desiccation technique and equipment for applying electrical energy to tissue to achieve superior thermal desiccative effects.

2. Description of the Prior Art

Electrosurgery involves the application of radio frequency electrical energy to tissue. The electrical energy originates from an electrosurgical generator (ESG) and is applied by an active electrode to the tissue. The active electrode typically has a small cross-sectional or limited surface area to concentrate the electrical energy at the surgical site. An inactive return electrode or patient plate contacts the patient at a remote location from the surgical site to complete the circuit through the tissue to the ESG. The patient plate is relatively large in size to avoid destructive energy concentrations. Alternatively, a pair of active electrodes may be used in a "bipolar" mode in which the electrosurgical energy flows directly through the tissue between the two active electrodes, and the electrosurgical effects are confined to the tissue directly located between the two closely-spaced electrodes.

A variety of different electrosurgical effects can be achieved, depending primarily on the characteristics of the electrical energy delivered from the ESG. Among the effects are a pure cutting effect, a combined cutting and hemostasis effect, a fulguration effect and a desiccation effect. Desiccation and fulguration are usually described collectively as coagulation. Many conventional ESG's offer the capability to selectively change the energy delivery characteristics and thus change the electrosurgical effects created.

Satisfactory fulguration effects have been particularly difficult to obtain. Some surgeons have preferred to use older spark gap generators known as "Bovie" devices for fulguration, but use other more modern ESG's for cutting or cutting with hemostasis. Indeed, spark gap ESG's have been the standard against which modern solid state ESG's have been measured for achievement of satisfactory fulguration effects. One modern ESG which achieves substantially improved fulguration effects, compared to both spark gap and previous solid state ESG's is described in U.S. Pat. No. 4,429,694, assigned to the assignee hereof. Despite the improvements available in fulguration, certain disadvantages remain for which there have been no satisfactory alternatives.

Conventional fulguration is characterized by electrical arcing through the air from various locations on the metal surface of the active electrode, with the arcs contacting the tissue in somewhat of a random nonpredictable manner. In many cases, arcs leave the active electrode in an initial trajectory traveling away from the tissue before actually curving around and striking the tissue surface. The result is an uneven, randomly concentrated or distributed delivery of arcing energy. An uneven eschar of variable characteristics is created on the surface of the tissue.

The random delivery of the arc energy creates holes which are significantly disparate in diameter (or cross-sectional size) and in depth. Larger, deeper holes are formed by repeated arcs contacting the tissue at approximately the same location. Smaller arc holes are also present in the tissue but they are unevenly distributed about the larger arc holes. The smaller arc holes are created by single individual arcs, or the less repetitious arcing to the tissue at the same location. The smaller arc holes are relatively small in diameter or cross-section and relatively shallow in depth, compared to the larger arc holes. Significant variations in cross-sectional size and depth between the large and small arc holes occur. Significant variations exist in the spacing and in the amounts of tissue between the large and small arc holes, causing the substantial variations in the surface distribution of the holes.

Thermal necrosis occurs in the tissue between the arc holes. The degree of thermal necrosis varies between total carbonization between the more closely spaced larger holes, to necrosis without charring or carbonization between the more widely separated smaller arc holes.

The eschar created has two distinct layers above the unaffected viable tissue. An arc hole reticulum of the tissue subjected to necrosis is created by the pattern of arc holes. The arc hole reticulum extends to greater depths in the areas of the deeper arc holes, and to substantially shallower depths in the areas of the shallower arc holes. Due to the random distribution and depth of the arc holes, the arc hole reticulum is relatively uneven in depth. Significant variations in the depth of the arc hole reticulum layer are typical. A layer of thermally desiccated tissue is located below the arc hole reticulum layer. Tissue necrosis in the thermally desiccated layer occurs as a result of the current heating effects of the electrical energy dissipating from the arcs. The desiccation layer is also uneven in depth and location due to the nonuniform application of the arcing energy over the arc hole reticulum layer. Significant variations in the depths of the desiccation layer are also typical.

Over a given area of tissue, certain locations are only moderately affected by the arcing energy. A thin arc hole reticulum and a thin desiccation layer result. Other areas have a relatively thick eschar formed therein. Very thick carbonized eschars tend to be fragile and are prone to crack when flexed, usually resulting in renewed bleeding from the unaffected tissue below the desiccation layer. Thin eschars are more flexible and therefore more desirable, but it has been difficult to obtain sufficient coagulation effects from thin eschars.

Causes of the uneven eschar created by prior fulguration techniques are not known with certainty, but numerous factors are theorized to play a role. One of the more significant contributory factors is probably changes in impedance in the arc pathway between the active electrode and the tissue. Impedance changes may result from variations in the distance which the arcs travel through the air, due to the changes in ionization potential between the active electrode and the tissue. It is virtually impossible for the surgeon to maintain the active electrode at a consistent distance from the tissue, particularly if the tissue is moving due to pulsation, or due to puckering and swelling as a result of applying the electrical energy. The arcing from random locations on the active electrode also creates different arc length pathways and hence impedances. The combined impedance of the tissue and the eschar changes with the application of electrical energy. The volatilization of the cells and vaporization of the moisture in the cells changes the relative impedance in a localized spot-to-spot manner on the surface of the tissue. The formation of the charred material also influences the arc pathways, presenting an opportunity for subsequent arcs to return to the tissue at the same location and thereby enlarge the pre-existing arc hole and create even further charring.

Another problem with conventional electrosurgery is that it is very difficult if not impossible to achieve effective fulguration on spongy or vascular tissue such as the liver or the spleen, or on other tissues from which there is a tendency for blood to continually ooze over the surface from the highly developed vascular network within the tissue. Often, only the surface of the oozing blood is coagulated, with no penetration to the surface of the tissue below the layer of blood. A superficial coagulum results on the surface of the blood, but this coagulum quickly sloughs away resulting in only temporary hemostasis. Of course, once the temporary coagulum sloughs away, bleeding continues. Even if a coagulation effect on the tissue surface can be established, it is easily destroyed or perforated by the arcs returning to the same locations causing the longer, deeper arc holes. The deeper arc holes perforate the eschar and extend into the viable tissue below the eschar to provide a pathway for continued bleeding. The heat created by the arcs causes boiling of moisture below the eschar, and the pressure of resulting vapor can also rupture the eschar to reinitiate bleeding.

Apart from the tissue disadvantages of conventional electrosurgical fulguration, certain other practical problems exist. Arcing from the active electrode rapidly increases the temperature of the active electrode. Electrode heating is responsible for a number of problems. If the heated active electrode contacts the tissue, as it inevitably will, or if the active electrode is immersed in fluid such as blood, proteins from the tissue or the blood are denatured and stick to the active surface of the electrode. The buildup of charred material on the electrode eventually creates a sufficiently high impedance so that adequate power can no longer be delivered. The surgeon must continually clean the electrode by wiping or scraping the charred material, which disrupts, distracts, and prolongs the surgical operation. Freshly created eschars can be detached in an effort to free a sticking electrode from the tissue surface. The random accumulation of charred material on the active electrode creates more random delivery of the arcing energy, even further increasing the random delivery pattern. Because of the variable nature of the impedance of the charred material, consistent power application is difficult or impossible. The accumulation of the charred material can obscure the surgeons view of the surgical site. The temperature of the active electrode may reach sufficiently elevated levels to transfer molten metal from the electrode to the patient, creating questionable effects. Because the electrode contacts the tissue, there is a potential for cross-contamination between viable tissues and diseased tissues. Although the clinical problems associated with cross contamination are not fully understood at the present time, the advantages of eliminating the possibility are evident. A significant smoke plume also results from the burning tissue because of the air environment in which the electrosurgery occurs. Not only does the plume produce a noxious odor, but there may be some evidence that particulates in the smoke plume from burning tissue may contain hazardous chemicals, virus, bacteria, neoplastic cells and other hazards. Of course, the oxygen environment in which the electrosurgery is conventionally conducted exhibits a potential for igniting paper drapes, surgical sponges and the like.

Some of the typical problems associated with creating and applying the arcs in conventional electrosurgery can be improved by optimizing the operating and other characteristics of the electrosurgical generator. U.S. Pat. No. 4,429,694 discloses an improved ESG which reduces some of the described disadvantages during fulguration. However, many of the disadvantages cannot be avoided and many of the characteristics cannot be improved by conventional electrosurgical techniques and equipment, due to the limitations previously inherent in electrosurgery.

The conventional technique of obtaining thermal desiccation by use of a conventional ESG is to apply electrical energy from a flat surface of the active electrode placed in contact with the tissue. An electrical resistance heating effect is created by the current flowing into the tissue from the active electrode. Because the active electrode contacts the tissue surface over a relatively large area, no arcing is intended to occur. To spread the thermal desiccation effect over a substantially large area, the active electrode is moved from location to location. It is very difficult to apply a level of energy which will obtain thermal desiccation but which will not cause the tissue to stick on the flat surface of the active electrode or arcing from the active electrode to non-contacted surface areas. The thermal desiccation effects are unevenly distributed because the active electrode is moved from spot to spot. Overlapping the spots of energy application can enhance the probability for tissue sticking and exaggerate the variable depth effects. Of course, moving the active electrode from spot to spot is very time consuming in an operation where time is very important or critical.

The prior art desiccation technique can only be applied to create surface desiccation effects. Furthermore, the inability to accurately control the amount of power, tissue sticking effects, and the like have prevented the prior use of electrosurgery on very thin fragile tissue such as the mesentary, and in other surgical techniques.

It is against this abbreviated background of previously existing disadvantages and problems in electrosurgery that the advantages and improvements of the present invention can be better appreciated.

SUMMARY OF THE INVENTION

In general, the electrosurgical technique and equipment for achieving coagulation in accordance with the present invention involves conducting a predetermined ionizable gas in a directed or generally laminar jet stream to the tissue at a predetermined flow rate sufficient to clear natural fluids from the tissue and to substantially expose the underlying tissue, while simultaneously conducting electrical energy at a predetermined primary radio frequency range in the gas jet stream through ionized conductive pathways. To achieve fulguration, the electrical energy is conducted as arcs in the ionized pathways. To achieve desiccation, the electrical energy is conducted in the ionized pathways as a non-arcing diffuse current.

The electrosurgical equipment of the present invention includes a nozzle which is removably mounted on a handle in a unique manner so as to be reliably sealed thereto to prevent the leakage of gas. The nozzle also supports an electrode along a small portion of its length so that a substantial portion of the electrode is exposed to the gas in a mixing chamber portion of the nozzle to improve initiation of the ionization of the gas.

The hose which supports the nozzle and the handle at a leading or free end thereof has its opposite end connected to a gas delivery apparatus by a connector element which also establishes a positive seal through a removable connection technique. The connector element is rotatably connected to the gas delivery apparatus in a manner so as to prevent the leakage of gas while permitting rotation of the hose to prevent kinks from forming in the hose as the surgeon is manipulating the handle and nozzle.

Many other significant features are inherent in the present invention, as well as many improvements over prior art coagulation techniques and equipment. These various features and improvements are discussed more completely in the following detailed description of the preferred embodiment taken in conjunction with the drawings.

DESCRIPTION OF THE PREFERRED EMBODIMENT

Figure 13:
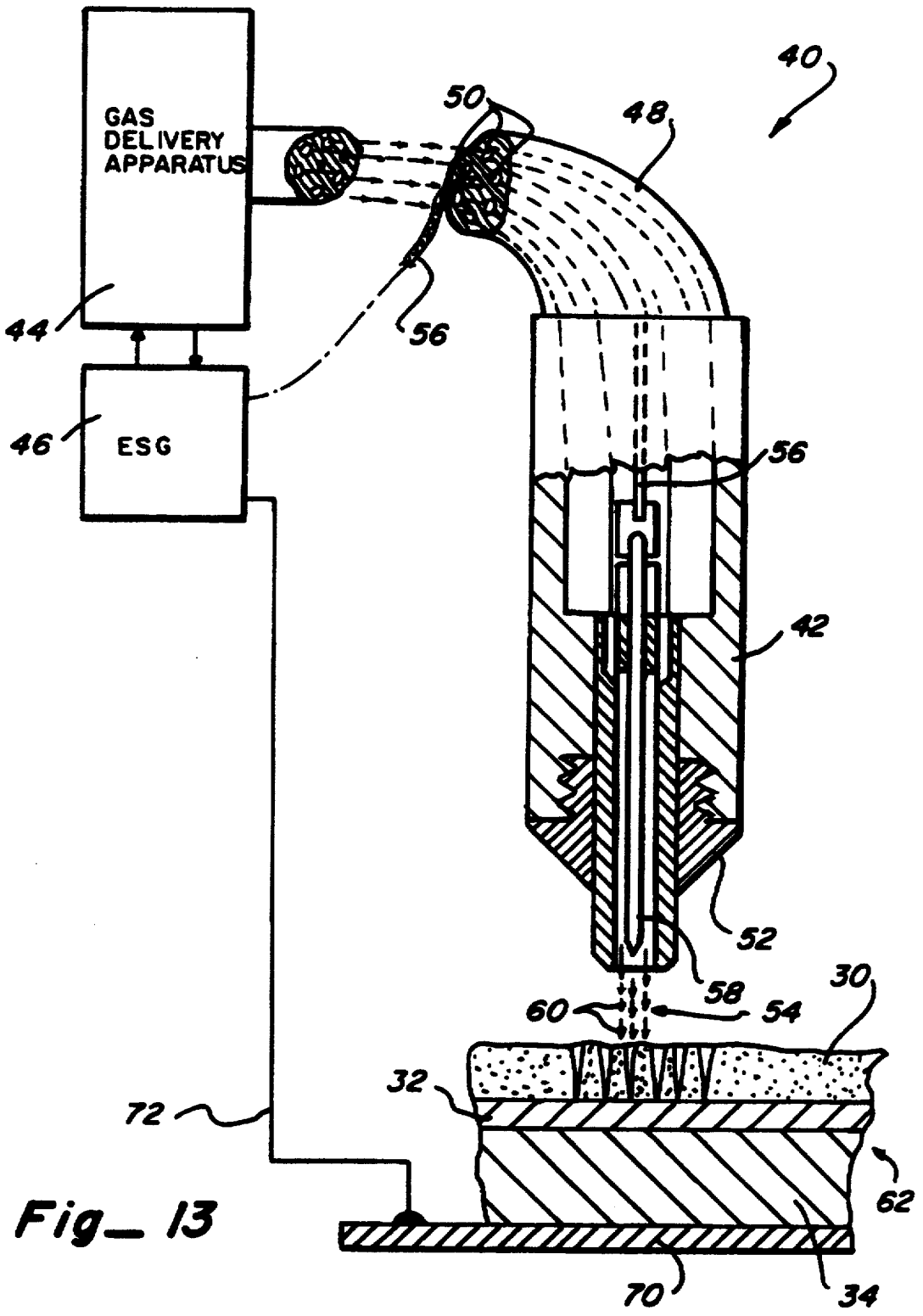
FIG. 13 is a generalized schematic view of an electrosugrical unit (ESU) embodying the present invention, illustrating an electrosurgical generator (ESG), a gas delivery apparatus, a segment of tissue shown illustratively in cross-section, and the elements of the invention shown in FIG. 1.

An electrosurgical unit (ESU) which embodies the present invention is shown generally in FIG. 13 and is referenced 40. The ESU 40 includes three major components, a pencil 42 which is *held and* manipulated by the surgeon, gas delivery apparatus 44 and an electrosurgical generator (ESG) 46. A flexible cord 48 connects the gas delivery apparatus 44 and the ESG 46 to the pencil 42. The gas delivery apparatus 44 delivers a preselected gas through a plurality of individual passageways or lumens 50 in the cord 48 to the pencil 42. The gas issues from a nozzle 52 of the pencil 42 in a directed or substantially laminar flow stream or jet 54.

The ESG 46 supplies electrical energy over a supply conductor 56 of the cord 48 to the pencil 42. The conductor 56 is electrically connected in the pencil to a needle-like electrode 58 which forms a part of the nozzle 52. The electrical energy supplied by the ESG 46 is of predetermined characteristic sufficient to ionize the gas flowing through the nozzle 52 and to create ionized pathways in the jet 54. The electrical energy travels in the ionized pathways in the jet 54 to a body tissue 62 where it creates a predetermined electrosurgical effect on the tissue 62.

In the fulguration mode of operation of the ESU, electrical energy is transferred in the ionized pathways in the form of arcs 60. The arcs 60 travel within the jet 54 until they reach the tissue 62 at the electrical surgical site. The jet 54 expands slightly above the surface of the tissue 62 and the arcs 60 disburse over a slightly enlarged area of the tissue surface compared to the cross-section of the jet 54. Electrical energy of the arcs is transferred into the tissue 62 and creates the upper arc hole reticulum or layer 30 and a desiccated layer 32 therebelow. The arc hole reticulum 30 and the desiccated layer are schematically illustrated in FIG. 13.

In the desiccation mode of operation of the ESU, the ionized pathways in the jet 54 transfer electrical energy from the electrode 58 as a non-arcing, conductive current. A gentle coupling effect is created at the tissue which does not cause holes in the tissue, because arcs are not present. As is described more completely in the parent application, Ser. No. 849,950, a desiccative electrosurgical effect is created, and only a desiccation layer similar to that schematically shown at 32 in FIG. 13 is formed on the surface of the tissue. The normal unaffected tissue structure such as that at 34 exists below the surface desiccated layer 32. The jet expands slightly at the surface of the tissue to couple the non-arcing electrical current over a slightly enlarged area of the tissue surface compared to the cross-sectional size of the jet. This type of desiccative coagulation electrosurgical effect has heretofore not been obtainable in the field of electrosurgery except through the apparatus disclosed in the parent application hereto. The desiccative effects on the tissue offer the possibility of accomplishing substantially new and different types of electrosurgical procedures by the use of an ESU.

The electrical energy delivered through the jet 54 travels through the tissue 62 to a return electrode or patient plate 70 which contacts the tissue 62. The patient plate 70 is connected by a return electrical conductor 72 to the ESG 46. A complete electrical circuit is thus established for conducting the energy from the ESG 46, to the pencil 42, through the jet 54, to and through the tissue 62, to patient plate 70, through the return conductor 72 to the ESG 46.

The pencil 42 includes a handle portion 76 and the nozzle 52 with the nozzle being threadedly connected to the handle for easy removal therefrom. As is best illustrated in FIGS. 2 and 5–8, the handle portion 76 of the pencil includes a generally cylindrical dielectric body 78 which may be ceramic. The cylindrical body 78 has a central axial passageway 80 therethrough which is relatively narrower at a leading end than at a trailing end as created by a relatively thick wall 82 at its leading end. The open landing end of the handle has internal threads 84 which form exemplary means for releasably [and connecting] receiving *and connecting* the nozzle 52 as will be described in more detail hereinafter.

Figure 5:
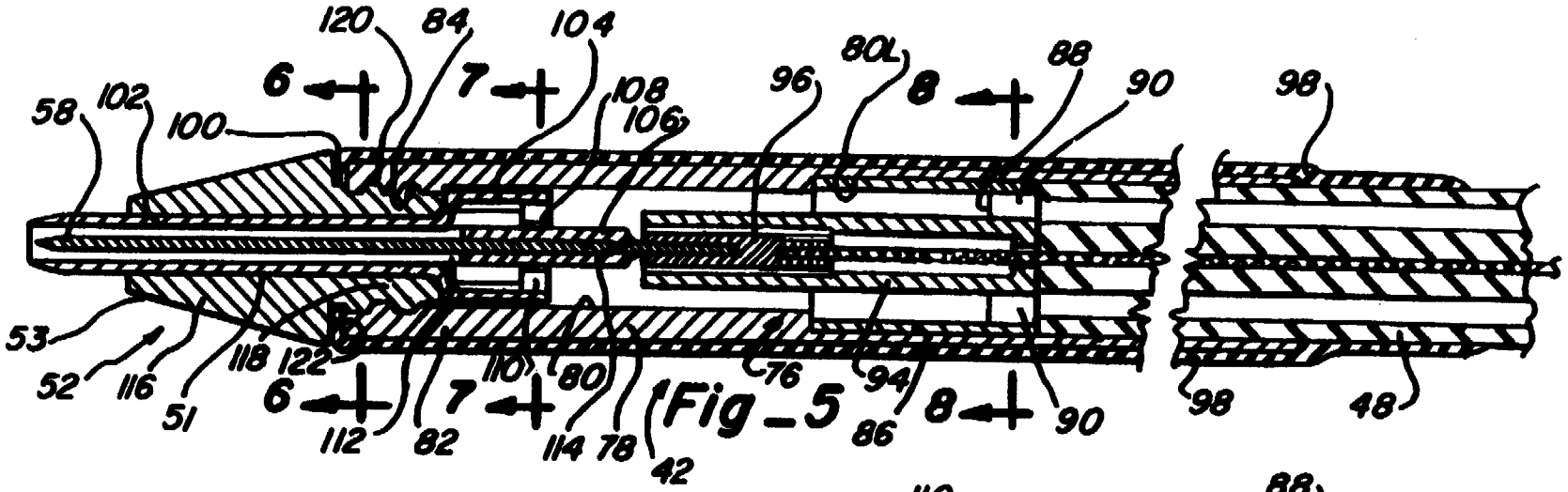
FIG. 5 is an enlarged section view of the nozzle and front end of the [hand piece] *handle* taken along line 5—5 of FIG. 1 with parts removed to condense the size.
Figure 8:
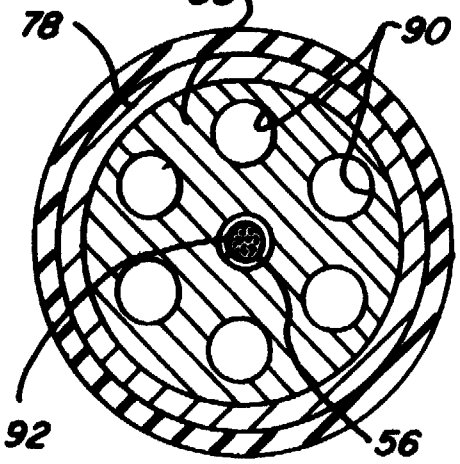
FIG. 8 is an enlarged section view taken along line 8—8 of FIG. 5.
Figure 7:
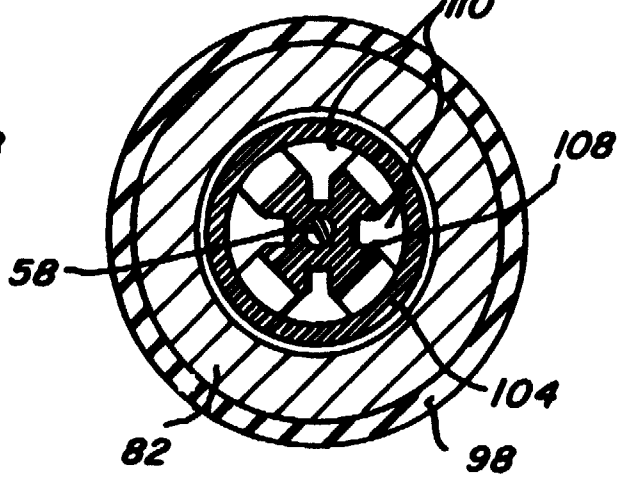
FIG. 7 is an enlarged section view taken along line 7—7 of FIG. 5.
Figure 6:
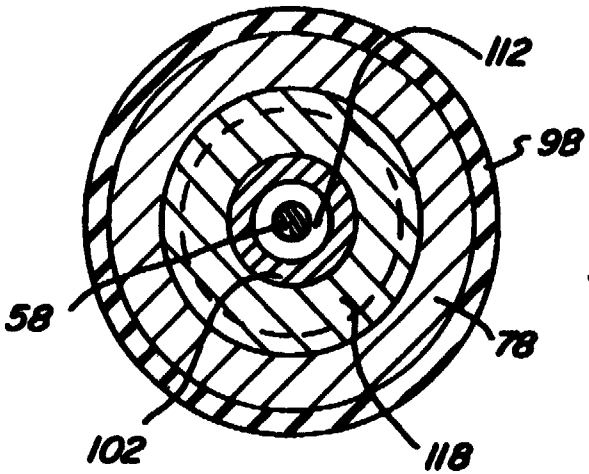
FIG. 6 is an enlarged section view taken along line 6—6 of FIG. 5.

A socket insert 86 is disposed internally of the handle portion 76 at the forwardmost extent of the large diameter portion 80L of the passageway through the handle. The socket insert 86, as is best illustrated in FIGS. 5 and 8, is also of cylindrical configuration having an outer diameter substantially the same as the inner diameter of the handle 76 at the location where the insert is positioned within the handle. At the trailing end of the socket insert 86, a disc-like wall 88 is formed having a plurality of circumferentially spaced openings 90 therethrough adapted to align with the passageways or lumens 50 through the hose 48. The wall 88 also has a central opening 92 therethrough adapted to accommodate the conductor 56 which passes through the hose and takes the form of a braided metal wire. A forwardly projecting internal cylindrical sleeve 94 projects forwardly from the disc-like wall 88 and confines and supports an electrical connector means such as a metallic socket 96 adapted to receive the electrode 58 of the nozzle as will be discussed later. The metallic socket 96 also includes a receptacle for receiving and retaining the leading end of the braided metal wire 56 which projects thereinto from the leading end of the hose 48.

The leading end of the hose 48 is also received in the enlarged diameter trailing portion 80L of the passageway 80 through the handle portion 76 and abuts the trailing end of the socket insert 86. The hose is aligned with the socket insert so that the passageways 50 through the hose are in alignment with the openings 90 through the disc-like wall 88 of the insert whereby gas can pass freely from the hose through the insert 86, *through the passageway 80 defined by the handle portion 76,* and subsequently through the nozzle. The hose is retained in its fixed relationship with the handle portion by an outer covering 98 which encompasses the handle portion 76 and overlaps a portion of the hose where the hose enters the trailing end of the handle portion. The covering 98 is of a soft pliable material such as silicone and also overlaps the leading end of the handle portion leaving the opening through the leading end of the handle portion unobstructed. It is important to note, however, that the covering does overlap the leading end of the handle forming a boot 100 which facilitates the establishment of a hermetic seal between the nozzle and the handle.

The nozzle 52 includes inner and outer dielectric component parts 51 and 53 with the electrode 58 being supported axially within the inner part. As mentioned previously, the nozzle is adapted to be releasably connected to the handle 76 to define the pencil 42. The inner part 51 of the nozzle has a forwardly projecting cylindrical-body 102, an integral intermediate enlarged cylindrical body 104 at the trailing end of the forwardly projecting cylindrical body 102, and an integral trailing cylindrical body 106 protruding rearwardly from the intermediate body. The intermediate body 104 at its trailing end has a plurality of inwardly directed ribs 108 which support the trailing body 106. The ribs 108 define passageways 110 therebetween through which gas is enabled to pass from the hose 48 through the socket insert [86 in] *86, into* the handle portion and subsequently through the passageways 110 for exposure to the electrode 58 within a nozzle passageway or mixing chamber 112 defined by the cylindrical inner spaces of the forward and intermediate bodys 102 and 104 respectively of the inner part 51. The trailing body 106 of the inner part has a cylindrical passage 114 therethrough adapted to mate with and receive the electrode 58 which is made of a conductive metal material and secured in the trailing body 106 in any suitable manner. The electrode 58 protrudes rearwardly from the trailing body of the inner part 51 so as to be receivable in the metal socket provided in the socket insert 86 of the handle portion. It is important to note that the trailing body of the inner part supports the electrode 58 along a small or minority portion of its length, and as such and in conjunction with the ribs are one example of support means for supporting the electrode. In a preferred embodiment, the support for the electrode extends only along a relatively short length of the electrode, for example, less than 20% of its length, exposing a significant portion of the electrode to the mixing chamber 112 and thus the gases flowing therethrough to improve initiation of the ionization of the gas. It has been determined that the initiation of the ionization process is facilitated by a greater exposure of the electrode to the gas jet stream 54 and for this reason, this feature of the invention is of significant value.

The outer part 53 of the nozzle 52 includes an enlarged frusto-conical head 116 and a trailing reduced diameter cylindrical portion 118 having external threads 120 adapted to mate with and be received in the internal threads 84 at the leading end of the handle portion. The outer part of the nozzle is affixed to and is unitary with the inner part 51 of the nozzle so that as the outer part is threaded into the leading end of the handle portion, the trailing end of the electrode 58 is inserted into the metallic socket in the handle portion in a positive manner. Also, it is important to note that the frusto-conical head 116 has a trailing circular radially disposed surface 122 which abuts with the boot 100 or overlapping portion of the handle cover to positively establish a hermetic seal between the nozzle and the handle portion. This seal is of critical importance in preventing the escape of gas and the possible transmittal of electrical energy to the surgeon's hand.

Figure 1:
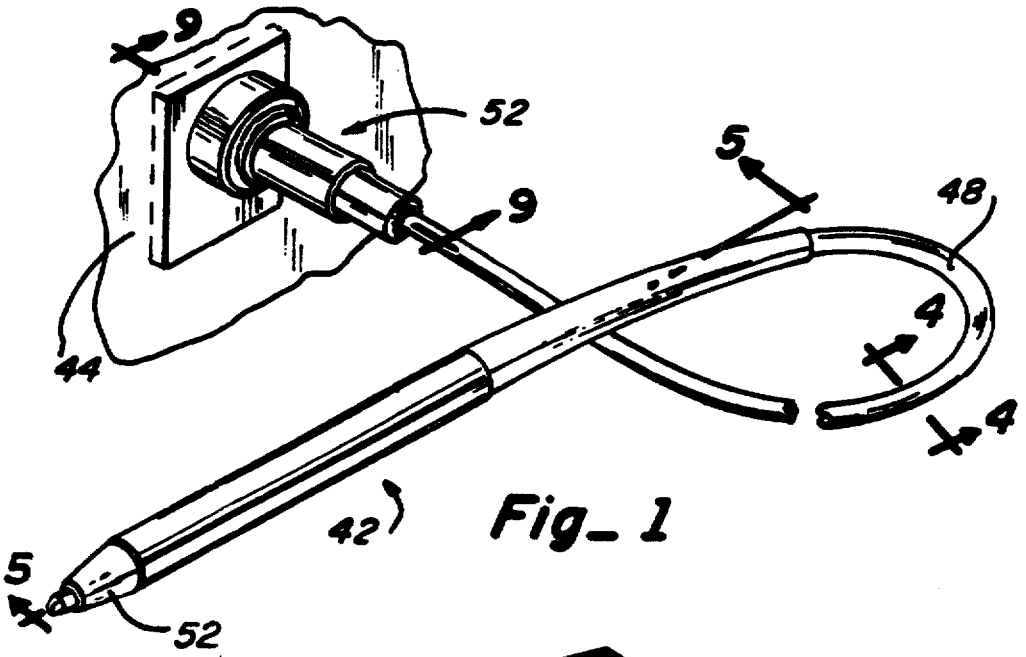
FIG. 1 is a perspective representation of a nozzle, [hand piece] *handle*, cord and connector of the present invention.
Figure 2:
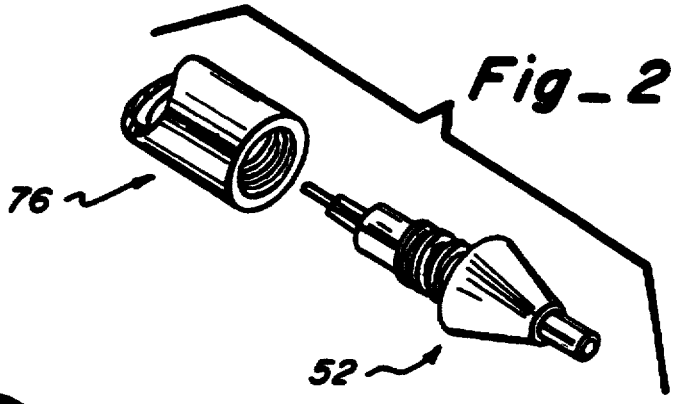
FIG. 2 is an enlarged exploded perspective view of the nozzle and the mating end of the [hand piece] *handle* illustrated in FIG. 1.
Figure 3:
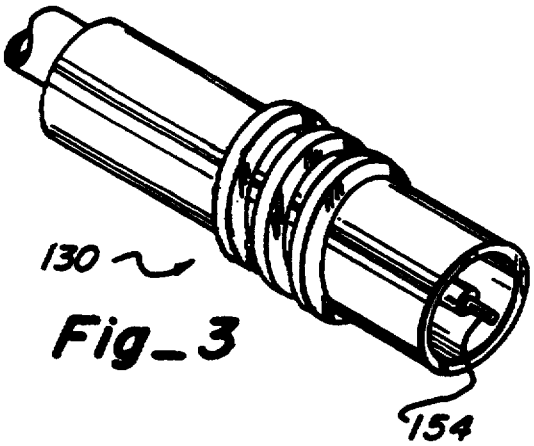
FIG. 3 is a fragmentary enlarged perspective view of the connector end of the cord illustrated in FIG. 1.
Figure 4:
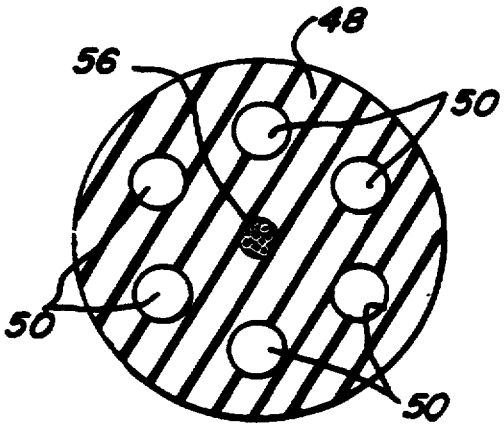
FIG. 4 is an enlarged section view of the cord taken along line 4—4 of FIG. 1.

The opposite or trailing end of the hose 48 is connected to the gas delivery apparatus 44 and the ESG 46 through a connector 124. The connector is best illustrated in FIGS. 3, [and] 9–12 *and 14* as including a female mating portion of member 126 which is directly fastenable to the gas delivery apparatus and ESG to receive gas and electrical energy therefrom and a male portion of member 128 secured in a unitary fashion to the trailing end of the hose. An intermediate sleeve member 130 is also provided which permits the hose to be positively secured to the female member 126 in a rotative relationship so that the hose will not form kinks as the pencil 42 is manipulated by a surgeon.

Figures 9, 10, 11, 12:
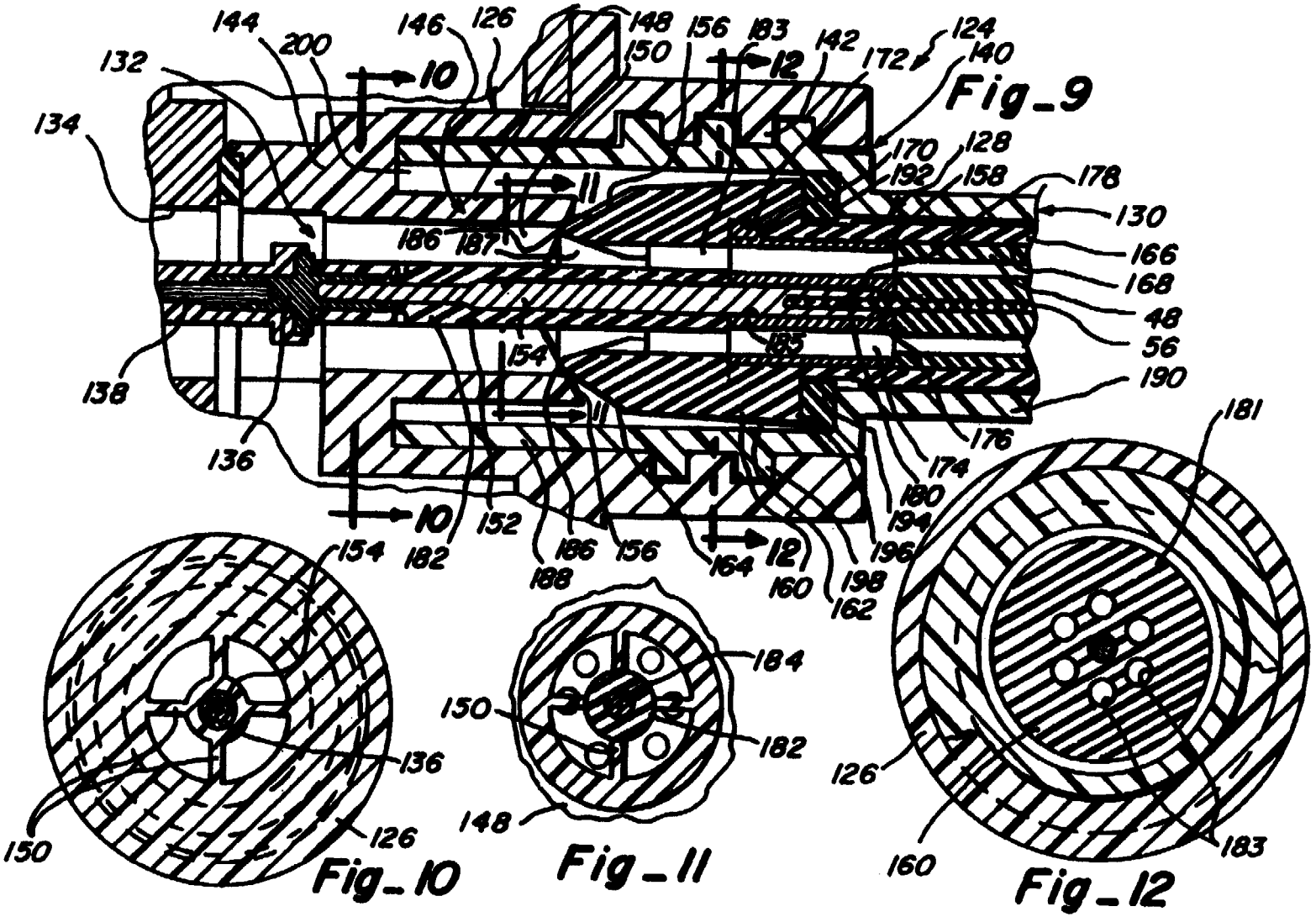
FIG. 9 is an enlarged section view of the connector taken along line 9—9 of FIG. 1.
FIG. 10 is a section view taken along line 10—10 of FIG. 9.
FIG. 11 is a section view taken along line 11—11 of FIG. 9.
FIG. 12 is a section view taken along line 12—12 of FIG. 9.
Figure 14:
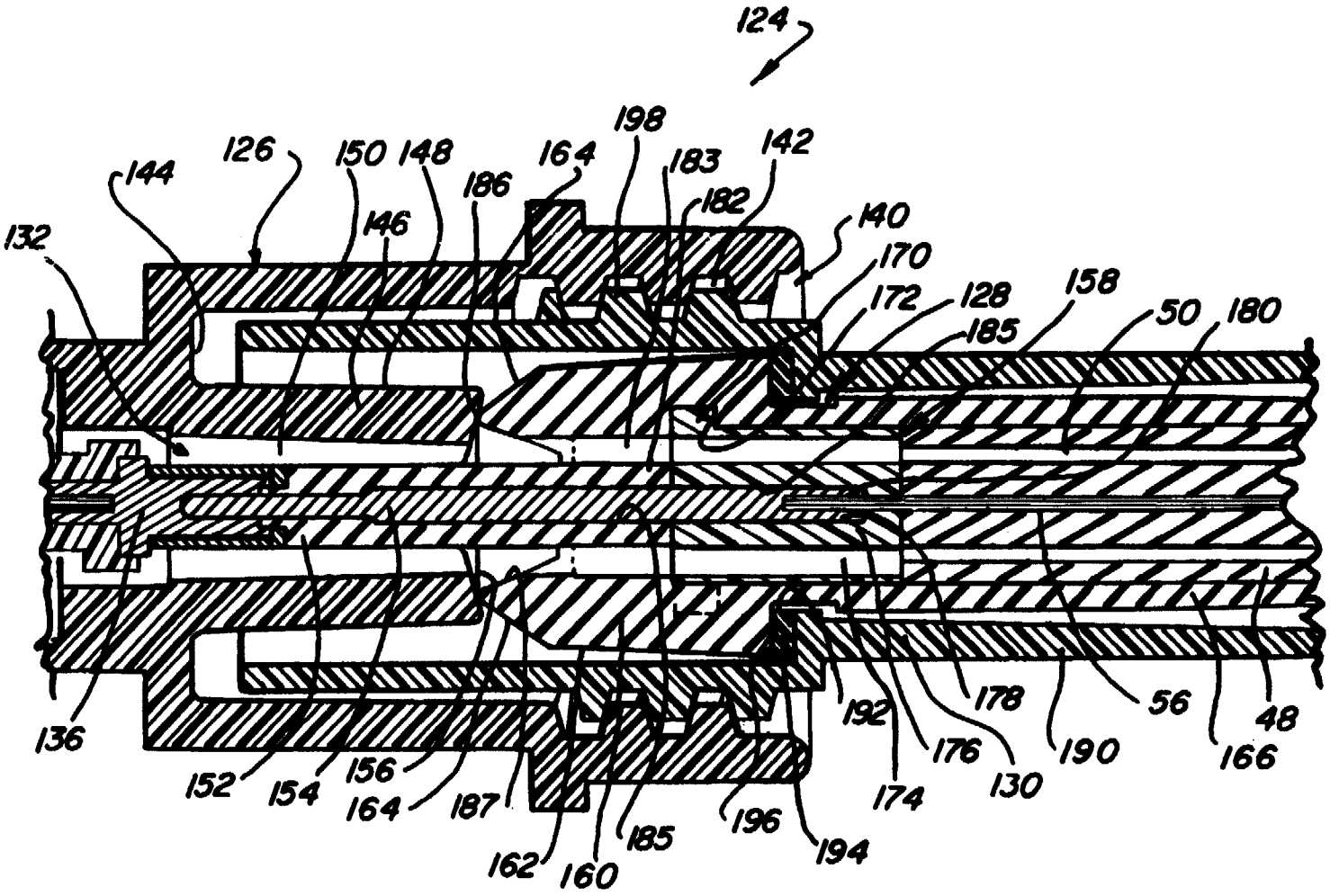
*FIG. 14 is an enlarged section view similar to FIG. 9, illustrating another configuration of the sealing elements of the connector.*

The female member 126 of the connector is probably best seen in [FIG. 9 and] *FIGS. 9 and 14* and is formed from a block of dielectric material such as plastic which is secured to the gas delivery apparatus 44 and ESG 46 such that a hollow interior passageway 132 through the female member can be aligned with a gas delivery opening 134 in the gas delivery apparatus and an electrical connector or contact means such as a metallic socket 136 which is in electrical communication with the ESG through a conductor 138. The female member is screwed or otherwise operatively secured to the gas delivery apparatus and ESG in a positive manner (not shown).

The female member 126 includes an outer cylindrical opening 140 adapted to receive the trailing end of the hose 48 with the opening 140 having internal threads 142 formed therein. A rear wall 144 of the female member supports a forwardly projecting central cylindrical hub 146 which extends into the cylindrical opening 140 in the female member for approximately a third of its length. The cylindrical hub 146 has a cylindrical wall 148 and a plurality of radial inwardly directed ribs 150 defining therebetween a central axial passage 152 for receiving an a connecting electrode 154 on the trailing end of the hose. The metallic socket 136 in the gas delivery apparatus and ESG protrudes forwardly into the central axis passage 152 in a position to receive the electrode 154 in a manner to be described hereinafter. The forward end of the cylindrical hub has a tapered surface 156 which is frusto-conical and rearwardly convergent and is continuous with the forward edges of the ribs at the locations where the ribs 150 are contiguous with the tapered surface 156. This frusto-conically tapered surface is adapted to cooperate with the trailing end of the hose in establishing a rotating hermetic seal as will become more clear later.

The male member 128 of the connector 124 includes a body made of a moderately resilient material such as rubber and an internal supporting insert 158 that is received within the body. The body has an enlarged head 160 defined by two axially aligned *tapered* frusto-conical surfaces 162 and 164 and a cylindrical extension portion 166 protruding forwardly away therefrom and adapted to receive the trailing end of the hose. The extension portion 166 has an internal cylindrical passageway 168 into which the hose 48 is inserted and retained in any suitable manner. The insert 158 is of generally cylindrical configuration having a protruding radial rib 170 around its trailing end which is adapted to be received within an annular recess 172 formed internally of the head 160. The seating of the radial rib 170 in the recess 172 retains the insert in a positive relationship with the male member. The insert has a plurality of openings 174 therethrough which are aligned with the passageways or lumens 50 through the hose so that gas can pass readily from the gas delivery apparatus 44 to the hose. The insert further includes an internal cylindrical sleeve 176 defining a cylindrical recess 178 in which the electrode 154 can be inserted and retained in any suitable manner. The electrode has a recess 180 defined in its leading end which is adapted to receive the end of the braided metal wire 56 that passes through the hose to establish an electrical connecting means and relationship between the braided metal wire and the electrode.

The enlarged head 160 includes a solid interior wall 181 having circular openings 183 therethrough in alignment with the openings 174 through the insert 158. The wall 181 is integral with and supports a rearwardly projecting cylindrical sleeve 182 through a plurality of ribs 184 shown best in FIGS. 9 and 11. The sleeve 182 has an internal passageway 185 therethrough which receives the electrode 154 in a manner such that the electrode protrudes a short distance from the rearward end of the sleeve. The male and female members 128 and 126 respectively of the connector are dimensioned such that the rearwardmost frusto-conical surface 164 on the head 160, which defines a generally circular trailing edge 186 of the head and a rearwardly opening frusto-conical recess 187, engages the cylindrical hub 146 of the female member when the electrode 154 is positively seated in the metal socket 136. The circular opening 183 and the recess 187 form a center opening for passing gas into the hose 48. The cylindrical hub of the female member engages the frusto-conical surface 164 at a circular edge or annular manner *as is shown in FIG. 9, or the circular edge 186 and the cylindrical hub 146 are compressed together at the frusto-conical surface 156 as shown in FIG. 14,* so as to establish a hermetic seal therewith *at these sealing edges and surfaces* and to allow the male member to rotate relative to the female member while maintaining that seal.

The male member 128 is positively retained in the female member 126 by the intermediate sleeve 130 which is of generally cylindrical configuration having a larger diameter trailing end 188 and a smaller diameter leading end 190. The smaller diameter leading end 190 is rotatably disposed about the cylindrical extension portion 166 of the male element and defines a radial abutment shoulder 192 against which is disposed a washer member 194 preferably made of a fluoroplasatic or other low friction material. The washer 194 fills a space between the radial abutment shoulder 192 on the intermediate sleeve and a radial shoulder 196 at the leading end of the enlarged head 160 of the male element so as to provide a low friction bearing surface between the intermediate sleeve and the male member. The large cylindrical end 188 of the intermediate sleeve has external threads 198 formed therein adapted to be received in the internal threads 142 of the female member and the portion of the sleeve rearwardly of the threads projects forwardly into a cylindrical socket 200 defined within the female member. The trailing end of the sleeve is adapted to abut the rear wall 144 of the female member when the sleeve 130 is fully threaded thereinto and at this same relative positioning of the intermediate sleeve with the female member, it will be appreciated that the male member is positively positioned relative to the female member as illustrated in FIG. 9 *and in FIG. 14* to establish the rotating seal between the male member and the female member along the frusto-conical surfaces 164 and 156. Also, the electrode 154 is positively positioned in the socket 136 of the gas delivery and ESG apparatus such that electricity is dependably transferred along the rear electrode 154 and the braided metal wire to the electrode 58 in the nozzle 52 as desired. Further, a clear passageway is established for the gas which emanates from the gas delivery apparatus and passes first through the female connector member and subsequently the male connector member and the hose for delivery to the nozzle.

It is important to note that the male member is easily connected to the female member through the threaded relationship of the female member with the intermediate sleeve 130 and that this connection permits full rotation of the hose relative to the female member while maintaining a hermetic seal to prevent the leakage of gas.

The electrosurgical unit 40 wherein described is used in accordance with the technique fully described in the aforenoted parent application which has been incorporated herein by reference and accordingly a description of that technique is not repeated.

Although the present invention has been described with a certain degree of particularity, it is understood that the present disclosure has been made by way of example, and changes in detail or structure may be made without departing from the spirit of the invention, as defined in the appended claims.

What is claimed is:

1. An electrosurgical unit for creating an eschar in the stroma of a tissue comprising in combination:

means for conducting a preselected gas in a jet stream to the tissue at a predetermined flow rate, means for transferring electrical energy at a preselected radio frequency range in ionized conductive pathways at a predetermined power level within the gas jet stream in an electrical circuit which includes the tissue to create the eschar, said means for conducting gas and said means for transferring electrical energy including a flexible hose, connector means having first and second connectable mating portions for connecting the hose to a source of gas and to a source of electrical energy, and nozzle means for delivering the gas jet stream and electrical energy to the tissue, said hose having at least one hose passageway therethrough for conducting gas and an electrical conductor means for conducting electrical energy therealong, a rear end of said hose comprising the first mating portion of said connector means, the first mating portion exposing a rear end of the electrical conductor means, the first mating portion including resilient material defining a [circular edge] *sealing surface*, the second mating portion of said connector means including a generally cylindrical element for contacting the [circular edge] *sealing surface* to establish a hermetic seal between said [circular edge] *sealing surface* and the cylindrical element when the first and second mating portions are connected, the second mating portion including an electrical connector means for connecting to said source of electrical energy and operative for contacting the rear end of said electrical conductor means when the first and second mating portions are connected, a front end of said hose comprising a handle having a front end to which said nozzle means is releasably connected, a nozzle electrical connector means connected to said electrical conductor means at the front end of said handle, a resilient boot on the handle which has a portion that overlaps the front end of the handle where said nozzle means connects, the operative connection of said nozzle means and said handle compressing the overlapping portion of the resilient boot to establish a hermetic seal between the nozzle means and the handle, said nozzle means including a nozzle passageway therethrough for directing gas from the hose passageway into the jet stream and also including an elongated electrode disposed in the nozzle passageway and having one end contacting the nozzle electrical connector means of the handle when the nozzle means is connected to the handle, and support means for supporting the elongated electrode within the nozzle passageway along a minority of the length of the electrode.

2. The electrosurgical unit defined in claim 1 wherein said support means supports the elongated electrode along less than one fifth of its length.

3. The electrosurgical unit defined in claim 1 wherein said support means includes a plurality of radially spaced ribs which support the elongated electrode and allow gas to pass therebetween for movement through the nozzle passageway.

4. The invention defined in claim 1 wherein the contacting relationship of the cylindrical element and the [circular edge] *sealing surface* permits relative rotation of the hose when the mating portions of the connector means are connected together.

5. The invention defined in claim 4 wherein the first mating portion includes a hollow [frustro-conical] *frusto-conical* member defining said [circular edge] *sealing surface* and within which said gas passes.

[6. For an electrosurgical unit for creating an eschar in the stroma of tissue, including means for conducting a predetermined gas in a jet stream to the tissue, means for transferring electrical energy at a predetermined radio frequency range in ionized conductive pathways within the gas jet stream in an electrical circuit which includes the tissue to create the eschar, said means for conducting gas and said means for transferring electrical energy including a flexible hose and connector means at one end of the hose for connecting the hose to a source of gas and a source of electrical energy, said hose having at least one hose passageway for conducting gas therethrough and an electrical conductor means for conducting the electrical energy therealong, and a handle connected at the other end of the hose; an improved nozzle means releasably connected to the handle and operative for delivering the gas from the hose passageway into the jet stream and for delivering electrical energy to the gas jet, said nozzle means comprising:

means defining a nozzle passageway for delivering the conducted gas as a jet stream to the tissue, an elongated electrode positioned in the nozzle passageway by which electrical energy is transferred in the jet stream, and support means for supporting the elongated electrode in the nozzle passageway along a minority of the length of the electrode.]

[7. The invention defined in claim 6 wherein said support means supports the elongated electrode along less than one fifth of its length.]

[8. The invention defined in claim 7 wherein said support means includes a plurality of radially spaced ribs which support the elongated electrode and allow gas to pass therebetween for movement through the nozzle passageway.]

[9. The invention defined in claim 6 further comprising:

a resilient boot connected to the exterior of the handle, the handle having a forward end to which said nozzle means is releasably connected, the resilient boot having an overlapping portion at the end of the handle which is resiliently compressed between the nozzle means and handle to establish a hermetic seal therebetween when the nozzle means and the handle are operatively connected.]

[10. The invention defined in claim 6 wherein said nozzle means further comprises:

an inner part including a forward cylindrical body extending coaxially along the electrode, an intermediate cylindrical body connected to the forward cylindrical body and defining a plurality of passageways for directing the gas to the interior of the forward cylindrical body, and a trailing body connected to the intermediate body and including said support means, the electrode being substantially unsupported in the forward cylindrical body.]

11. For an electrosurgical unit for creating an eschar in the stroma of tissue which includes means for conducting a predetermined gas in a jet stream to the tissue, means for transferring electrical energy at a preselected radio frequency range in ionized conductive pathways within the gas jet stream in an electrical circuit which includes the tissue to create the eschar, said means for conducting gas and said means for transferring electrical energy including a flexible hose, and nozzle means connected at one end of the hose for delivering the gas jet stream and electrical energy to the tissue, said hose having at least one passageway therethrough for conducting gas and an electrical conductor means for conducting the electrical energy therealong; an improved connector connected to the other end of the hose and having first and second mating portions *including first and second electrical connector means respectively* for connecting the other end of the hose to a source of the predetermined gas and a source of electrical energy, said improved connector comprising:

[a first] *said second* mating portion defining a forwardly-projecting generally-circular hub, the hub also defining a forward facing [frustro-conical] *frusto-conical* surface, the hub having a hollow interior through which the gas is conducted, and [a first] *said second* electrical connector means positioned within the hollow interior of the hub by which to conduct the electrical energy from the source of electrical energy, the hollow interior and the [first] *second* electrical connector means being located coaxially with respect to the [frustro-conical] *frusto-conical* surface;

[a second] *said first* mating portion adapted to be connected to the [first] *second* mating portion, the [second] *first* mating portion including a body defining a rearwardly-projecting head having at least one [frustro-conical shaped] *sealing* surface formed thereon and shaped to contact and seal against the [frustro-conical] *frusto-conical* surface of the [first] *second* mating portion upon connection of the mating portions, the head also having a center opening located coaxially with respect to the [frustro-conical] *frusto-conical and sealing* surfaces, the center opening passing the gas from the [first] *second* mating portion to the passageway in the hose, and [a second] *said first* electrical connector means for contacting said [first] *second* connector means and conducting electrical energy from said [first] *second* connector means to the electrical conductor means of said hose; and the [frustro-conical surfaces] *frusto-conical surface of the second mating portion and the sealing surface* of the *first* mating [portions] *portion* engage and seal with one another at an annular location surrounding the path through which the gas flows from the hollow interior of the hub to the center opening of the head when the first and second mating portions are connected together.

12. The invention defined in claim 11 wherein the head of the [second] *first* mating portion is formed of resilient material, and the sealing of the [frustro-conical] *frusto-conical and sealing* surfaces is established by compression of the head at the annular location.

13. The invention defined in claim 11 wherein the engagement of the [frustro-conical] *frusto-conical and sealing* surfaces at the annular location permits relative rotation of the hub and the head while maintaining the seal.

14. The invention defined in claim 11 wherein the body includes a forwardly-projecting extension portion having a receiving passageway therein for receiving the hose and into which the hose is received.

*15. The invention as defined in claim 1 wherein the sealing surface of the first mating portion is compressed against the cylindrical element.*

*16. The invention as defined in claim 15 wherein the sealing surface of the first mating portion includes a circular edge, the cylindrical element includes a sealing surface which substantially faces the first mating portion, and the circular edge is compressed against the sealing surface of the cylindrical element.*

*17. The invention as defined in claim 16 wherein the sealing surface of the cylindrical element includes a frusto-conical surface tapering in a direction away from the first mating portion, and the circular edge is compressed against the frusto-conical sealing surface of the cylindrical element.*

*18. The invention defined in claim 11 wherein:*

*the sealing surface of the first mating portion is formed on the exterior of the head; and wherein:*

*the sealing surface of the first mating portion engages and seals with the frusto-conical surface of the second mating portion at an interior edge of the frusto-conical surface of the second mating portion.*

*19. The invention defined in claim 11 wherein:*

*the sealing surface of the first mating portion is formed by a circular edge on the head; and wherein:*

*the circular edge engages and seals with the frusto-conical surface of the second mating portion.*

*20. For an electrosurgical unit for creating an eschar in the stroma of tissue, including means for conducting a predetermined gas in a jet stream to the tissue, and means for transferring electrical energy at a predetermined radio frequency range in ionized conductive pathways within the gas jet stream in an electrical circular which includes the tissue to create the eschar, said means for conducting gas and said means for transferring electrical energy including a flexible hose and connector means at one end of the hose for connecting the hose to a source of gas and a source of electrical energy, said hose having at least one hose passageway for conducting gas therethrough and an electrical conductor means for conducting the electrical energy therealong, and a handle connected at the other end of the hose; an improved nozzle means releasably connected to the handle and operative for delivering the gas from the hose*

*passageway into the jet stream and for delivering electrical energy to the gas jet, said nozzle means comprising:*

*means defining a nozzle passageway for delivering the conducted gas as a jet stream to the tissue;*

*an elongated electrode positioned in the nozzle passageway by which electrical energy is transferred in the jet stream;*

*support means for supporting the elongated electrode in the nozzle passageway along a minority of the length of the electrode; and*

*a resilient boot connected to the exterior of the handle, the handle having a forward end to which said nozzle means is releasably connected, the resilient boot having an overlapping portion at the end of the handle which is resiliently compressed between the nozzle means and handle to establish a hermetic seal therebetween when the nozzle means and the handle are operatively connected.*

*21. For an electrosurgical unit for creating an eschar in the stroma of tissue, including means for conducting a preselected gas in a jet stream to the tissue at a predetermined flow rate, and means for transferring electrical energy at a predetermined radio frequency range in ionized conductive pathways within the gas jet stream in an electrical circuit which includes the tissue to create an eschar; said means for conducting gas and said means for transferring electrical energy including a flexible hose having at least one hose passageway for conducting gas along the hose and having an electrical conductor for conducting electrical energy along the hose, a connector having a first mating portion and a second mating portion adapted to be connected to one another, the first mating portion connected to a rear end of the hose and attached to the electrical conductor, the second mating portion adapted to be connected to a source of the predetermined gas to be conducted into the hose passageway and to a source of the electrical energy to be conducted along the electrical conductor, the first and second mating portions each including an electrical contact adapted to contact the electrical contact of the other mating portion upon connection of the first and second mating portions, the electrical contacts of the connected mating portions establishing electrical conductivity between the electrical energy source connected to the second mating portion and the electrical conductor connected to the first mating portion, and a pencil connected at a front end of the hose for receiving the gas from the hose passageway and the electrical energy from the electrical conductor and for establishing the gas jet and for delivering the electrical energy in the gas jet; improvements comprising:*

*the first mating portion including material defining a sealing surface adapted to connect with an element of the second mating portion to establish an hermetic seal between the sealing surface and the element upon connection of the first and second mating portions;*

*the first and second mating portions defining an interior gas flow opening extending between the connected mating portions through which the gas flows from the gas source to each hose passageway;*

*the mating portions position the electrical contacts substantially in the interior gas flow opening with the interior gas flow opening substantially surrounding the electrical contacts;*

*the hermetic seal surrounds and encloses the interior gas flow opening and the electrical contacts upon connection of the mating portions;*

*said pencil comprising a handle formed of dielectric material and an interior passageway formed in and extending along the handle, the hose connected to a rear end of the handle and the hose passageway communicating with the interior passageway to flow gas from the hose passageway into the interior passageway; and*

*said pencil further comprising a nozzle assembly connected at a front end of the handle, the nozzle assembly comprising an elongated solid metallic electrode and a generally cylindrical nozzle passageway formed of dielectric material, the nozzle passageway conducting the gas from the interior passageway within the handle into a generally laminar flow jet stream, a support positioning the electrode coaxially within the nozzle passageway and extending the electrode rearwardly from the nozzle passageway into the interior passageway in the handle, a forward portion of the electrode within the nozzle passageway being fully exposed to the flow of gas passing through the nozzle passageway, the support located rearwardly of the nozzle passageway within the interior passageway, a rear end of the electrode connected to the electrical conductor within the interior passageway, the position of the electrode within the nozzle passageway creating a substantially unobstructed space surrounding the electrode within the nozzle passageway for delivering electrical energy to pass gas within substantially all of the nozzle passageway.*

*22. The invention defined in claim 21 wherein the support contacts the elongated electrode along less than one fifth of the length of the electrode.*

*23. The invention defined in claim 21 wherein the support includes a plurality of radially positioned ribs which extend outward from the electrode to support the electrode and allow gas to pass therebetween for movement into the nozzle passageway.*

*24. The invention defined in claim 21 wherein the support includes a cylindrical body surrounding the electrode and extending axially along a portion of the length of the electrode.*

*25. The invention defined in claim 24 wherein:*

*the cylindrical body extends less than one fifth of the length of the electrode and terminates at a position forward of the rear end of the electrode; and*

*the interior passageway includes a plurality of passageways exterior of the cylindrical body for conducting the gas from the interior passageway around the cylindrical body and into the nozzle passageway.*

*26. The invention defined in claim 21 wherein the hermetic seal established by the connection of the mating portions permits relative rotation of the mating portions.*

*27. The invention defined in claim 21 wherein the first mating portion includes a frusto-conical member defining the sealing surface on the exterior of the frusto-conical member, the frusto-conical member also having an internal opening which defines a part of the interior gas flow opening.*

*28. The invention defined in claim 21 wherein the material defining the sealing surface is resilient.*

*29. The invention defined in claim 28 wherein:*

*the pencil further comprises a resilient material between the front end of the handle and the connected nozzle assembly to establish a hermetic seal between the nozzle assembly and the front end of the handle.*

*30. The invention defined in claim 21 wherein the material defining the sealing surface is compressible against the element upon connecting the first and second mating portions.*

*31. The invention defined in claim 21 wherein the nozzle assembly is releasably connected to the front end of the handle.*

*32. The invention defined in claim 21 wherein:*

*the nozzle assembly is releasibly connected to the front end of the handle; and*

*the pencil further comprises a resilient boot on the handle including a portion overlapping the front end of the handle and which is compressed by the connection of the nozzle assembly to establish a hermetic seal between the nozzle assembly and the handle.*

*33. For an electrosurgical unit for creating an eschar in the stroma of tissue, including means for conducting a preselected gas in a jet stream to the tissue at a predetermined flow rate, and means for transferring electrical energy at a predetermined radio frequency range in ionized conductive pathways within the gas jet stream in an electrical circuit which includes the tissue to create the eschar; said means for conducting gas and said means for transferring electrical energy including a flexible hose having at least one hose passageway for conducting gas along the hose and having an electrical conductor for conducting electrical energy along the hose, a connector having a first mating portion and a second mating portion adapted to be connected to one another, the first mating portion connected to a rear end of the hose and attached to the electrical conductor, the second mating portion adapted to be connected to a source of the predetermined gas to be conducted into the hose passageway and to a source of the electrical energy to be conducted along the electrical conductor, the first and second mating portions each including an electrical contact adapted to contact the electrical contact of the other mating portion upon connection of the first and second mating portions, the electrical contacts of the connected mating portions establishing electrical conductivity between the electrical energy source connected to the second mating portion and the electrical conductor connected to the first mating portion, and a pencil connected at a front end of the hose for receiving the gas from the hose passageway and the electrical energy from the electrical conductor and for establishing the gas jet and for delivering the electrical energy in the gas jet; improvements in the connector comprising:*

*the first mating portion including material defining a sealing surface adapted to connect with an element of the second mating portion to establish an hermetic seal between the sealing surface and the element upon connection of the first and second mating portions;*

*the first and second mating portions defining an interior gas flow opening extending between the connected mating portions through which the gas flows from the gas source to each hose passageway;*

*the mating portions position the electrical contacts substantially in the interior gas flow opening with the interior gas flow opening substantially surrounding the electrical contacts; and*

*the hermetic seal surrounds and encloses the interior gas flow opening and the electrical contacts upon connection of the mating portions.*

*34. The invention defined in claim 33 wherein:*

*the first mating portion further comprises a rearwardly-projecting head defining the sealing surface thereon, the head also defining an internal opening which defines a part of the interior gas flow opening.*

*35. The invention defined in claim 34 wherein the head has a generally frusto-conically shaped exterior and the sealing surface is formed on the exterior of the head.*

*36. The invention defined in claim 35 wherein the head includes resilient material and the hermetic seal is established by compression of the head at the location of the hermetic seal.*

*37. The invention defined in claim 35 wherein:*

*the second mating portion includes a forwardly-projecting hub having a forward facing frusto-conically shaped surface defining the element, the hub having an internal opening which defines a part of the interior gas flow opening which conducts the gas from the source of gas to the internal opening of the first mating portion; and*

*the hermetic seal is located on the forward facing surface defining the element of the second mating portion.*

*38. The invention defined in claim 37 wherein:*

*the sealing surface is established at an edge of one of the frusto-conical surfaces of one of the first or second mating portions and at the frusto-conical surface of the other one of the first or second mating portions.*

*39. The invention defined in claim 33 wherein:*

*the first mating portion further comprises a head having resilient material defining the sealing surface, the head also defining an internal opening which defines a part of the interior gas flow opening;*

*the second mating portion includes a forwardly-projecting hub having a forward facing sealing surface defining the element, the hub defining an internal opening which defines a part of the interior gas flow opening through which the gas is conducted from the source of gas to the first mating portion, and;*

*the hermetic seal is established by compression of the sealing surface of the head against the sealing surface of the hub.*

*40. The invention defined in claim 39 wherein the sealing surface of the head comprises a circular edge.*

*41. The invention defined in claim 39 wherein the seal is established at an edge of one of the sealing surfaces of the head and the hub.*

*42. For an electrosurgical unit for creating an eschar in the stroma of tissue, including means for conducting a preselected gas in a jet stream to the tissue at a predetermined flow rate, and means for transferring electrical energy at a predetermined radio frequency range in ionized conductive pathways within the gas jet stream in an electrical circuit which includes the tissue to create the eschar; said means for conducting gas and said means for transferring electrical energy including a flexible hose having at least one hose passageway for conducting gas along the hose from a source of gas, the hose further having an electrical conductor for conducting electrical energy along the hose from a source of electrical energy, and a pencil connected at a front end of the hose for receiving the gas from the hose passageway and the electrical energy from the electrical conductor, the pencil including a receptacle at a forward end of the pencil and a nozzle assembly releasably attached within the receptacle, the nozzle assembly comprising a nozzle for creating the gas jet stream from the gas received in the pencil and an elongated electrode positioned in the nozzle for delivering the electrical energy received in the pencil in the gas jet; an improvement to said nozzle assembly comprising:*

*a unitary part having a forward cylindrical body, an intermediate body connected to the forward body and a trailing body connected to the intermediate body, the forward and intermediate and trailing bodies all formed integrally of a dielectric material, the forward body defining a cylindrical nozzle passageway for delivering the gas as a generally laminar jet stream,*

*the intermediate body extending rearwardly from the forward body and defining a chamber adjacent a rear end of the nozzle passageway for communicating the gas into the nozzle passageway, the chamber having a substantially larger cross section than the nozzle passageway, the trailing body extending inwardly from a rear of the intermediate body and defining a support for retaining the elongated electrode within the nozzle assembly, the elongated electrode extending from a forward end located substantially at a forward end of the nozzle passageway to a rear end located rearwardly beyond a rearwardmost portion of the support, the support surrounding the electrode and extending forwardly from the trailing body within the chamber to a location short of the nozzle passageway, the support positioning the elongated electrode substantially coaxially in the nozzle passageway, the support surrounding the electrode along less than one fifth of its length and exposing the electrode within the nozzle passageway to the flow of gas therearound.*

*43. The invention defined in claim 42 wherein the electrode is supported in the nozzle assembly solely by the support.*

*44. The invention defined in claim 42 wherein the trailing body is connected to the intermediate body by a plurality of radially positioned ribs which allow gas to pass therebetween for movement through the nozzle passageway.*

*45. The invention defined in claim 42 wherein the unitary part is an inner part of the nozzle assembly, and further comprising:*

*an outer part supporting and retaining the unitary part in a connected relationship with the pencil.*

* * * * *